United States Patent
Peters

(10) Patent No.: US 10,449,281 B2
(45) Date of Patent: Oct. 22, 2019

(54) METHOD AND DEVICE FOR CREATING TURBULENCE BY PULSATING FLOW

(71) Applicant: Fresenius Medical Care Deutschland GmbH, Bad Homburg (DE)

(72) Inventor: Arne Peters, Bad Homburg (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 329 days.

(21) Appl. No.: 14/902,705

(22) PCT Filed: Jul. 2, 2014

(86) PCT No.: PCT/EP2014/064020
§ 371 (c)(1),
(2) Date: May 10, 2016

(87) PCT Pub. No.: WO2015/000934
PCT Pub. Date: Jan. 8, 2015

(65) Prior Publication Data
US 2016/0250403 A1    Sep. 1, 2016

(30) Foreign Application Priority Data
Jul. 2, 2013    (DE) .................. 10 2013 011 010

(51) Int. Cl.
*A61M 1/16*    (2006.01)
*A61M 1/34*    (2006.01)
(Continued)

(52) U.S. Cl.
CPC .......... *A61M 1/1603* (2014.02); *A61M 1/267* (2014.02); *A61M 1/342* (2013.01);
(Continued)

(58) Field of Classification Search
CPC .............. A61M 1/1603; A61M 1/3458; A61M 1/3672; A61M 1/267; A61M 1/342;
(Continued)

(56) References Cited

U.S. PATENT DOCUMENTS 4,821,761 A  *  4/1989  Aid .................... A61M 1/1656
                                                    137/101.21
8,123,396 B1      2/2012  Karpetsky et al.
(Continued)

FOREIGN PATENT DOCUMENTS

DE            10205056        8/2003
WO       WO 03/095982        11/2003
(Continued)

*Primary Examiner* — Walter D. Griffin
*Assistant Examiner* — Shuyi S. Liu
(74) *Attorney, Agent, or Firm* — Jacobson Holman, PLLC.

(57) ABSTRACT

A method and a device use pulsed flow profiles in the addition of a solution to an extracorporeal circulation to improve the mixing of the added solution with the blood, in particular in regional anticoagulation with citrate. Extracorporeal blood treatment processes are usually carried out with anticoagulation of the blood. In regional anticoagulation with citrate, sometimes a clot is observed in the extracorporeal blood circulation at the point of addition of the calcium infusion solution. If the extracorporeal circulation becomes occluded, the treatment must be interrupted. To prevent this, the method and device add the calcium infusion solution with a pulsed flow profile, with which better mixing is achieved.

18 Claims, 2 Drawing Sheets

(51) Int. Cl.
*A61M 1/36* (2006.01)
*A61M 5/142* (2006.01)
*A61M 5/168* (2006.01)
*B01F 15/02* (2006.01)
*B01F 5/04* (2006.01)
*A61M 1/26* (2006.01)
*A61M 39/10* (2006.01)

(52) U.S. Cl.
CPC ........ *A61M 1/3458* (2014.02); *A61M 1/3672* (2013.01); *A61M 1/3675* (2013.01); *A61M 5/142* (2013.01); *A61M 5/16827* (2013.01); *A61M 39/10* (2013.01); *B01F 5/0471* (2013.01); *B01F 15/024* (2013.01); *A61M 2205/3334* (2013.01); *A61M 2205/502* (2013.01); *A61M 2206/10* (2013.01); *A61M 2206/16* (2013.01); *A61M 2206/20* (2013.01)

(58) Field of Classification Search
CPC .... A61M 1/3675; A61M 39/10; A61M 5/142; A61M 5/16827; A61M 2205/3334; A61M 2205/502; A61M 2206/20; A61M 2206/16; A61M 2206/10; B01F 5/0471; B01F 15/024

USPC ........................................................ 604/506
See application file for complete search history.

(56) References Cited

U.S. PATENT DOCUMENTS

| | | | | |
|---|---|---|---|---|
| 2007/0062861 | A1* | 3/2007 | Lannoy | A61M 1/342 210/501 |
| 2011/0168614 | A1* | 7/2011 | Pouchoulin | A61M 1/342 210/134 |
| 2011/0257522 | A1* | 10/2011 | Berard-Andersen | A61M 5/16859 600/438 |
| 2014/0044568 | A1* | 2/2014 | Fouillet | F04B 43/046 417/63 |

FOREIGN PATENT DOCUMENTS

| | | | |
|---|---|---|---|
| WO | WO 2009/030973 | 3/2009 | |
| WO | WO 2010/029401 | 3/2010 | |
| WO | WO 2010029417 A2 * | 3/2010 | ............ A61M 1/342 |
| WO | WO 2012104072 | 8/2012 | |

\* cited by examiner

METHOD AND DEVICE FOR CREATING TURBULENCE BY PULSATING FLOW

BACKGROUND OF THE INVENTION

1. Field of Invention

The invention relates to the use of pulsed flow profiles in the addition of solutions to the extracorporeal circulation to improve the mixing of the added solution with the blood, in particular in regional anticoagulation with citrate.

2. Description of the Prior Art

WO 2009/030973 describes a blood tubing system having an infusion site with a constriction. This constriction serves to create turbulence in this infusion site.

WO 2010/029401 A1 and WO 2012/104072 A1 describe methods for controlling a blood treatment machine for performing regional anticoagulation with citric acid.

STATEMENT OF PROBLEM

In extracorporeal treatment of blood, infusion solutions or medications are infused into the patient, usually through the extracorporeal blood circulation, i.e., the tubing system that is used, Depending on the type of infusion solution, rapid mixing of the infusion solution with the blood may be desirable.

It is standard to administer infusion solutions for inhibiting the coagulation of blood in extracorporeal treatment of blood in order to prevent a possible occlusion in the blood tubing system.

Mainly two methods are used for this purpose, the systemic and the regional anticoagulation methods, In regional anticoagulation, a citrate solution, which complexes calcium and thus suppresses the coagulation of blood, is generally used as the anticoagulant. Before returning the blood to the patient, the physiological concentration of free calcium must be restored because side effects occur if the calcium levels are too low. Therefore, in regional anticoagulation, a solution containing calcium is added to the blood before reinfusion into the patient, so that the calcium concentration and thus the coagulation ability of the blood are restored at the same time.

The infusion of infusion solutions or medications into the tubing system of the extracorporeal blood circulation usually takes place through addition sites in a T-shaped connection, so called T-sections. Laminar flow conditions prevail in these T-sections because of the circular cross section and the smooth inside wall at the addition point. In addition, the flow rates of the infused solutions are low in comparison with the blood flow rate.

The largely laminar flow conditions and the low flow rates of the infusion solutions or medications flowing into the bloodstream may result in poor mixing of the blood with the added infusion solution. This inadequate mixing of the two fluids at the addition site is undesirable, especially in the addition of calcium solution to blood, and in isolated cases it may even lead to the formation of clots downstream, which can in turn lead to an occlusion in the extracorporeal blood circulation under unfavorable circumstances.

To prevent this, rapid and homogeneous mixing of the added calcium solution with the blood is desirable.

However, this problem can also occur in the addition of other fluids, e.g., medications, where a rapid mixing effect may be advantageous.

This problem is known in the state of the art, and special addition sites containing means for creating turbulence have been described to solve this problem.

SUMMARY OF THE INVENTION

The object of the present invention is to provide a method and a device which will permit rapid and homogeneous mixing of the two fluids combined in the T-section even when using a standard blood tubing system with standard T-sections and without any special means for creating turbulence.

According to the teaching of the present invention, this object is achieved by a method and by a device as described herein. Specific embodiments of the invention are also described herein.

SUMMARY OF THE INVENTION

The present invention consists of a method for mixing blood with an infusion solution A in a T-section of a tubing system for an extracorporeal blood circulation. In the tubing system, the blood is pumped by a first pump in the main line and the infusion solution A is pumped by a second pump out of a branch line and into the main line through the T-section, In doing so, the second pump is controlled or regulated by the control unit in the method according to the invention, in such a way that the second pump delivers the infusion solution A with a pulsed flow profile. The pulsed flow profile is created by the control signals of the control unit in a targeted manner.

In the case of a pulsed flow profile, there is periodic alternation of the phases during which the fluid or the infusion solution is being pumped (flow pulses or pulses) and phases during which no fluid or definitely less fluid is being pumped (flow pauses), thus yielding a so-called pulsed flow profile. In other words, the second pump runs discontinuously, which means that there are relevant changes in the delivery rate of the second pump, so the pump is not necessarily stopped at periodic intervals.

The pulsed flow profile may have a rectangular profile, but a sinusoidal profile, a needle-shaped profile or the like is also suitable.

In the case of a rectangular profile, the pulsed flow profile is defined on the basis of the pulse width (duration of pump operation or of the pumping of the fluid) Tau2, the pulse pause (duration of the pump standstill) Tau1, the resulting pulse frequency f and the quantity of liquid pumped in a pulse per unit of time or the pump rate, the pulse flow rate (Vopt), It is also conceivable that the pump does not come to a standstill in the pulse pause but instead continues to run at a much lower pumping rate, This would then have to be taken into account in the calculation of the average pump rate. The aforementioned parameters yield as a result the average flow rate or the average pump rate (Vm) of the fluid or of the infusion solution A over a longer interval of time.

With the method according to the invention, the extracorporeal blood circulation has one or more branch lines in addition to the main line carrying the blood, and these branch lines may be connected by T-sections to the blood circulation, T-Sections are plastic parts having three openings, which are connected by a T-shaped fluid line, The fluid line may also have a y-shaped shaped design or something Similar. T-Sections may be glued into a tubing system as an insertion piece, so that the main line of the tubing system, e.g., the line carrying the blood, can be connected to a branch line. Infusion solutions can be infused through these branch lines into the blood in the extracorporeal circulation.

In one embodiment of the method according to the invention, the control unit can control or regulate the first pump, so that it runs continuously to pump the blood at a steady flow rate, It is self-evident for those skilled in the art that flow changes may occur or become necessary during a treatment due to external circumstances, but these flow changes should not have a negative effect on the basic functioning of the method.

For those skilled in the art, it is also self-evident that pressure pulses and flow pulses may occur due to the structure of the pumps, e.g., occlusion pumps, This flow profile, which is automatically created by the pump structure, is not covered by the present invention.

In one embodiment of the method according to the invention, at least one additional infusion solution B may be pumped by a third pump out of another branch line and into the main line of the tubing system.

The method according to the invention and the device according to the invention are advantageous when an especially effective mixture of two solutions is to be achieved in a tubing system.

In an extracorporeal blood treatment, the flow rate of the infused solution into the blood (infusion solution or medication) is determined by the desired dosing.

The dose of a substance used in the extracorporeal blood treatment may be determined by the treating physician. However, suggestions for the dosing can be stored in the control unit of the treatment machine.

The dosing in the extracorporeal blood treatment may be defined by a certain ratio of the blood flow rate to the flow rate (Vm) of the infusion solution. The mixing effect cannot be improved by increasing the steady flow rate because then the dosing would no longer be correct.

Through the use of a pulsed flow profile at a fixed dose, which is defined by the average flow rate (Vm), the pulse flow rate (Vopt) can be decoupled from the average flow rate (Vm) because this is obtained from the pulse flow rate (Vopt) and/or the pulse width (Tau2) and/or the pulse frequency f and thus can be adjusted at an optimal flow rate (Vopt) for the mixture by means of the pulse width (Tau2) and/or pulse frequency f.

In a rectangular profile in which no fluid is pumped in the pulse pause, this yields, for example:

$$(Vm)=f*Tau2*Vopt \qquad (1)$$

The method according to the invention and the device according to the invention are advantageous in particular when used in regional anticoagulation to achieve a particularly effective mixture of the blood with the solutions for regional anticoagulation.

Regional anticoagulation with citrate is a conventional method in which the method according to the invention is preferably to be used. In this case, a citrate-containing infusion solution, e.g., a 4% $Na_3$ citrate solution, is pumped into the blood in the main line by a third pump through a branch line. Since this infusion solution inhibits the coagulation of blood, this branch line is situated near the blood withdrawal site of the extracorporeal circulation, i.e., near the arterial needle. The citrate complexes the calcium contained in the blood, thereby inhibiting the ability of the blood to coagulate. If a dialyzer having a semipermeable membrane is present in the extracorporeal blood circulation, for example, then the citrate together with the bound calcium is removed from the blood through this membrane.

The calcium in the blood is complexed and the calcium bound to citrate is also removed from the blood in the dialyzer in dialysis methods, so before returning the blood to the patient, the free calcium concentration (not the complexed calcium) must be brought back to a physiological range, If the calcium concentration is too low, it may lead to adverse effects during the treatment. To restore the physiological calcium concentration, a calcium infusion solution may be infused into the patient's blood through an additional site, e.g., in the form of a T-section, which is provided in the blood circulation in proximity to the venous patient access.

Use of the method and device according to the present invention is especially advantageous here because poor mixing of blood with the calcium solution can result in the formation of clots in the T-section and occlusion of the extracorporeal circulation.

In one embodiment of the method according to the invention, the infusion solution A is a solution containing calcium. In another embodiment of the method according to the invention, the infusion solution B is an infusion solution containing citric acid.

In one embodiment of the method according to the invention, the pumps used in the method are controlled or regulated by a control unit, so that they supply the steady flow rates or pump rates and pulsed flow profiles used in the method.

In one embodiment of the method according to the invention, at least one pump is controlled or regulated by the control unit to pump the blood in the extracorporeal circulation and a second pump is controlled or regulated to pump an infusion solution A, for example, an infusion solution containing calcium.

In one embodiment of the method according to the invention, a third pump is also controlled or regulated by the control unit to pump an additional infusion solution B, for example, an anticoagulant solution such as an infusion solution containing citric acid.

In one embodiment of the method according to the invention, the control unit is configured so that it controls or regulates the flow of the second and/or the third pump, which is dependent on the first pump that serves to pump the blood in the extracorporeal circulation.

In one embodiment of the method according to the invention, the control unit may be configured so that it automatically adjusts the flow rate of the second and/or third pump(s) when there are changes in the blood flow rate.

In one embodiment of the method according to the invention, the control unit is configured to calculate a pulsed flow profile consisting of the pulse flow rate (Vopt), a pulse width (Tau2) and a pulse frequency f from the average flow rate (Vm) of the infusion solution, which is obtained from the desired dosage, using an algorithm stored in the memory, such that the infusion solution is pumped at a pulsed flow rate (Vopt), which leads to better mixing of the infusion solution A.

This pulsed flow profile may be used automatically or may be displayed as a suggestion on a user interface, which (suggestion) must then be confirmed by the user.

In an alternative embodiment of the method according to the invention, some or all of the parameters of the pulsed flow profile, pulse flow rate (Vopt) and/or pulse width (Tau2) and/or pulse frequency f and/or flow rate in the pulse pause may be entered on a user interface and sent to the control unit.

In one embodiment of the method according to the invention, these working parameters, i.e., the flow rates or pump rates of some or all of the pumps may be transmitted to the control unit via a user interface. The user can enter the working parameters, e.g., the blood flow rate, the flow rate of the anticoagulant and/or the flow rate of the second fluid, e.g., the infusion solution containing calcium, on this user interface. The data may then he transmitted to the control unit, which then controls or regulates the pumps accordingly.

In addition, there is also the possibility that the control unit receives the working parameters that are used during the treatment through signals from the pumps and then can adapt the flow rate of the anticoagulant and/or the second fluid to the infusion solution containing calcium, for example.

In one embodiment of the method according to the invention, some of the working parameters may also be calculated by a calculation unit. This calculation unit may be part of the control unit. The calculation unit may also be a separate device, which is connected to the control unit. For example, an algorithm may be stored in the calculation unit to calculate the flow rate of the anticoagulant after defining the desired blood flow rate or determining the currently prevailing blood flow rate.

In one embodiment of the method according to the invention, the calculation unit may also calculate the average volume flow of the second fluid, e.g., the infusion solution containing calcium, from the values for the blood flow rate and/or the anticoagulant flow rate. It is also possible for the calculation unit to calculate a pulsed flow profile from the average volume flow of the second fluid, e.g., the infusion solution containing calcium. The calculation unit determines or then proposes values for the pulse width (Tau2), the pulse frequency f and the pulse flow rate (Vopt), An algorithm that calculates these values so that the desired average volume flow is obtained may be used to do so.

Alternatively, the parameters of pulse width (Tau2), pulse frequency f and pulse flow rate (Vopt) may be defined by the user and transmitted to the control unit and/or the calculation unit via the user interface.

In the method according to the invention, the pulsed flow profile may be a plug-type profile, With a plug-type profile, the pulse flow rate (Vopt) of the infusion solution A is greater than the blood flow rate, which yields very short pulse widths because the average flow rate Vm of the infusion solution is much lower than the blood flow rate.

In one embodiment, the pulse flow (Vopt) amounts to 1.1 to 2 times the blood flow rate, preferably 1.3 to 1.7 times the blood flow rate.

Values for the blood flow rate in an extracorporeal blood treatment may be 100 to 600 mL/min, preferably 150-300 mL/min.

Values for the average flow rate of the infusion solution (Vm) may be 50-300 mL/h, preferably 90-150 mL/h.

The values for the pulse width may then be between 10 and 100 ms, preferably 20-50 ms for the plug-shaped profile.

The values for the pulse frequency f are then obtained from equation (1).

With short pulse widths (e.g., >50 ms), control of the flow is not simple. In one embodiment of the invention, the pump is triggered in such a way that it pumps a certain volume per pulse.

Control of the pump rate may then be omitted. The pulse frequency and/or the pulse volume are varied. The average flow rate is controlled via the pulse frequency and the pulse volume, Alternatively, the pulsed flow may have a rippling profile, where the pulse flow rate (Vopt) and the blood flow rate are of the same order of magnitude, with the pulse flow rate typically being smaller than the blood flow rate.

In one embodiment, the pulse flow rate (Vopt) is 0.1 to 1 times the blood flow rate, preferably 0.4-0.6 times the blood flow rate.

Values for the blood flow rate in an extracorporeal blood treatment may amount to 100 to 600 mL/min, preferably 150-300 mL/min.

The values for the average flow rate of the infusion solution (Vm) may be 50-300 mL/h, preferably 90-150 mL/h.

The values for the pulse width may then be between 0.1 and 5 s, preferably 0.3-3 s for the rippling profile.

The values for the pulse frequency f were obtained from equation (1).

The average flow rate here is controlled via the pulse flow rate, the pulse frequency and/or the pulse volume.

Any pumps known in medical technology may be used in this method. The pump used to pump the blood must be suitable specifically for pumping blood. Any occlusion pump may he used for infusion solutions A and B. In one embodiment, these are peristaltic pumps. In an alternative embodiment, they are diaphragm pumps.

In one embodiment, the extracorporeal circulation of the process may be used for extracorporeal treatment of a patient's blood, preferably a dialysis treatment. A dialysis treatment may be a hemodialysis treatment, a hemofiltration treatment and/or a hemodiafiltration treatment.

The invention also relates to a device for extracorporeal treatment of blood, comprising at least one first pump for pumping blood and a second pump for pumping an infusion solution A plus at least one control unit, which regulates or controls the second pump, so that the second pump delivers the infusion solution A with a pulsed flow profile. The pulsed flow profile is created in a targeted manner by the control signals of the control unit.

In a pulsed flow profile, there is a periodic alternation of the phases in which the liquid or the infusion solution is pumped (pulses or flow pulses) and phases in which no fluid or definitely less fluid is pumped (flow pauses), thus resulting in a so-called pulsed flow profile. In other words, the second pump runs discontinuously, which means that there are relevant changes in the delivery rate of the second pump, and the pump is not necessarily stopped at periodic intervals.

The pulsed flow profile may have a rectangular profile but a sinusoidal profile, a needle-shaped profile (delta or Dirac function) or the like is also suitable.

In the case of a rectangular profile, the pulsed flow profile is defined by the pulse width (duration of the pump operation or of the pumping of the fluid) Tau2, the pulse pause (duration of the pump standstill) Tau1, the resulting pulse frequency/and the quantity of fluid pumped per unit of time in the pulse or the pumping rate, the pulsed flow rate (Vopt). It is also conceivable that the pump does not come to a standstill during the pulse pause but instead continues to run at a much lower pumping rate. This would then have to be taken into account in the calculation of the average pumping rate. The average flow rate or the average pumping rate (Vm) of the liquid phase or of infusion solution A over a longer interval of time is obtained from the parameters given above.

In one embodiment of the device according to the invention, the control unit controls or regulates the first pump which pumps the blood, so that the first pump runs continuously to pump the blood at a steady flow rate.

It is self-evident for those skilled in the art that flow changes may occur or may become necessary during a treatment due to external circumstances but these do not interfere with the basic functioning of the method.

It is also self-evident for those skilled in the art that pressure pulses and flow pulses may occur due to the structure of the pumps. This flow profile created by the pump structure is not covered by the present invention.

In one embodiment, this device is suitable for performing an extracorporeal blood treatment with regional anticoagulation. The device may then have another pump, i.e., a third pump for pumping an additional fluid, an infusion solution B, preferably an anticoagulant. For this embodiment, the third pump is then designated as the anticoagulant pump. This anticoagulant is preferably a solution containing citric acid and/or citrate. In regional anticoagulation with a solution containing citric acid and/or citrate, the infusion solution A which serves to neutralize the anticoagulant is preferably an infusion solution containing calcium. In this embodiment, the second pump is designated as a calcium pump.

In one embodiment, the additional pump, i.e., the third pump, preferably the anticoagulant pump is also controlled or regulated by the control unit. The additional pump, the third pump, preferably pumps the anticoagulant continuously at a steady flow rate. Alternatively, the anticoagulant may also be pumped with a pulsed flow profile.

In regional anticoagulation in the extracorporeal circulation, it is advantageous to coordinate the pump rates of the three pumps that are used, namely the blood pump, the anticoagulant pump and the calcium pump with one another.

In one embodiment, the control unit is designed to take into account the working parameters or delivery rate of the first pump, the blood pump, in regulating or controlling the second pump, preferably the calcium pump, and the third pump, preferably the anticoagulant pump.

In one embodiment of the device according to the invention, the control unit is configured to calculate a pulsed flow profile consisting of the pulse flow rate (Vopt), a pulse width (Tau2) and a pulse frequency f from the average flow rate (Vm) of the infusion solution, which is obtained from the desired dosage using a stored algorithm; this is the pulse frequency at which the infusion solution A is pumped with a pulse flow rate (Vopt) which leads to better mixing of the infusion solution A with the blood.

This pulsed flow profile may be used automatically or may be displayed as a suggestion on a user interface, but this suggestion must then be confirmed by the user.

In one alternative embodiment of the device according to the invention, a user interface may be provided, on which all the parameters or individual parameters of the pulsed flow profile, the pulse flow rate (Vopt) and/or the pulse width (Tau2) and/or the pulse frequency f and/or the flow rate in a pulse pause and the working parameters, i.e., the flow rates or pump rates of all the pumps or individual pumps may be input and can be sent to the control unit.

On this user interface, the user may then enter the working parameters, for example, the blood flow rate, the flow rate of the anticoagulant agent and/or the flow rate of the second fluid, for example, the infusion solution containing calcium. This data may then be transmitted to the control unit which then regulates or controls the pumps accordingly.

In addition, there is also the possibility that the control unit receives the working parameters that are in effect during the treatment through signals from the pumps and then can adjust the flow rate of the anticoagulant agent and/or of the second fluid, e.g., the infusion solution containing calcium accordingly.

In one embodiment of the device according to the invention, at least some of the working parameters of the pumps and/or the parameters of the pulsed flow profile can also be calculated by a calculation unit. This calculation unit may be part of the control unit. The calculation unit may also be a device having a separate design which is connected to the control unit. For example, an algorithm may be stored in the calculation unit, so that the flow rate of the anticoagulant is calculated after the desired blood flow rate has been defined or after the currently prevailing blood flow rate has been determined.

In one embodiment of the device according to the invention, the calculation unit may also calculate the average volume flow of the second fluid, for example, the infusion solution containing calcium, from the values for the blood flow and/or the anticoagulant flow. It is also possible that the calculation unit calculates a pulsed flow profile from the average volume flow of the second fluid, for example, the infusion solution containing calcium. The calculation unit then determines or suggests values for the pulse width (Tau2), the pulse frequency f and the pulse flow rate (Vopt). An algorithm that calculates these values to yield the desired average volume flow may be used for this purpose.

Alternatively, the parameter of pulse width (Tau2), pulse frequency f and pulse flow rate (Vopt) may be defined by the user and transmitted to the control unit and/or calculation unit via the user interface.

In one embodiment, the device according to the invention can generate a pulsed flow profile as a plug-type profile.

In a plug-type profile, the pulsed flow (Vopt) of the infusion solution A is greater than the blood flow, which results in very short pulse widths because the mean flow Vm of the infusion solution is much lower than the blood flow.

In one embodiment, the pulsed flow (Vopt) amounts to 1.1 to 2 times the blood flow, preferably 1.3 to 1.7 times the blood flow.

Values for the blood flow in an extracorporeal blood treatment may be 100 to 600 mL/min, preferably 150-300 mL/min.

Values for the mean flow of the infusion solution (Vm) may be 50-300 mL/h, preferably 90-150 mL/h.

The values for the pulse width could then be between 10 and 100 ms, preferably 20-50 ms for the plug-type profile.

The values for the pulse frequency f are then derived from equation (1).

At short pulse widths (e.g., >50 ms), it is not easy to control the flow. In one embodiment of the invention, the pump is controlled so that it delivers a certain volume per pulse. Control of the delivery rate can then he omitted. The pulse frequency and/or the pulse volume are varied. The mean flow rate is controlled via the pulse frequency and pulse volume.

Alternatively, in one embodiment, the pulsed flow created by the device according to the invention may have a crimped flow profile, The pulsed flow (Vopt) here and the blood flow are of the same order of magnitude; typically the pulsed flow is lower than the blood flow.

In one embodiment, the pulsed flow (Vopt) amounts to 0.1 to 1 times the blood flow, preferably 0.4-0.6 times the blood flow.

Values for the blood flow in an extracorporeal blood treatment may be 100 to 600 mL/min, preferably 150-300 mL/min.

Values for the mean flow of the infusion solution (Vm) may be 50-300 mL/h, preferably 90-150 mL/h.

The values for the pulse width may then amount to between 0.1 and 5 s, preferably 0.3-3 s, for the crimped flow profile.

The values for the pulse frequency f are then obtained from equation (1).

The mean flow rate is controlled here through the pulsed flow, the pulse frequency and/or pulse volume.

The flow profile created by the calculation unit may be displayed for the user on a user interface and executed by the latter only after confirmation.

In one embodiment of the device, the second pump may be a peristaltic pump.

In an alternative embodiment of the device, the second pump may be a diaphragm pump.

In one embodiment, the device for extracorporeal blood treatment may he for example a machine for hemodialysis, hem filtration and/or hemodiafiltration. The device may be suitable for performing one or more of these types of treatment.

BRIEF DESCRIPTION OF THE DRAWINGS

Additional details and advantages of the invention are described in further detail on the basis of the exemplary embodiments depicted in the drawings, which show.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Figure 1:
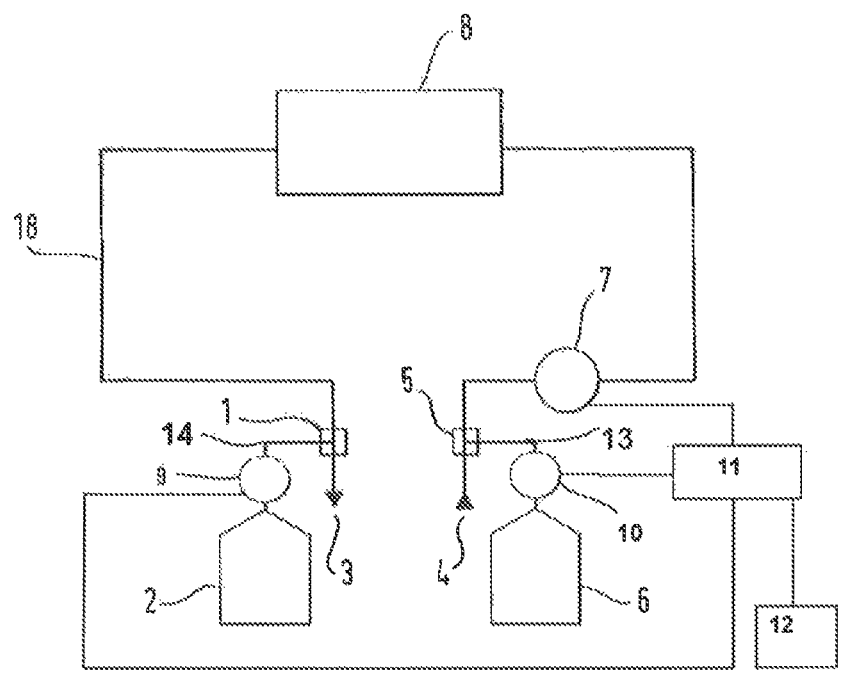
FIG. 1: a schematic diagram of an extracorporeal circulation with regional anticoagulation and a control unit for implementing the method according to the invention

FIG. 1 shows schematically a blood circulation suitable for performing the method. according to the invention, Blood is pumped by the blood pump 7 from the arterial patient access 4 through the main line 18 of the tubing, system of the extracorporeal circulation with the dialyzer 8. Upstream from the blood pump 7, a first addition point 5 in the form of a conventional T-section is provided in the main line 18 of the extracorporeal circulation. An anticoagulant 6, shown here in the form of a citrate bag, is added at this first addition point 5 through the branch line 13 via another pump 10, where the citrate bag contains 4% $Na_3$ citrate, for example, which is infused into the main line 18 of the extracorporeal blood circulation. A second addition point 1 in the form of an additional conventional T-section is located in the immediate vicinity of the venous patient access 3, where an infusion solution A2, in the form of a calcium solution here, is added to the blood through a branch line 14 through the second pump 9.

The user can enter treatment parameters, including the desired blood flow rate, the desired citrate flow rate and the desired calcium dosing via the user interface 12. The user can select different options for the pulsed flow profile of the pumps 7, 9 and 10. The user interface 12 may also serve to display data for the user.

The data is transmitted between the user interface 12 and the control unit 11. The control unit 11 then controls or regulates the pumps 7, 9 and 10. The control unit 11 can calculate the citrate dosing and the calcium dosing from the data for the blood flow. Then a calculation unit (not shown) calculates a pulsed flow profile from the calcium dose entered by the user. If there are changes in a parameter during a treatment, the pulsed flow profile may be recalculated.

Figure 2:
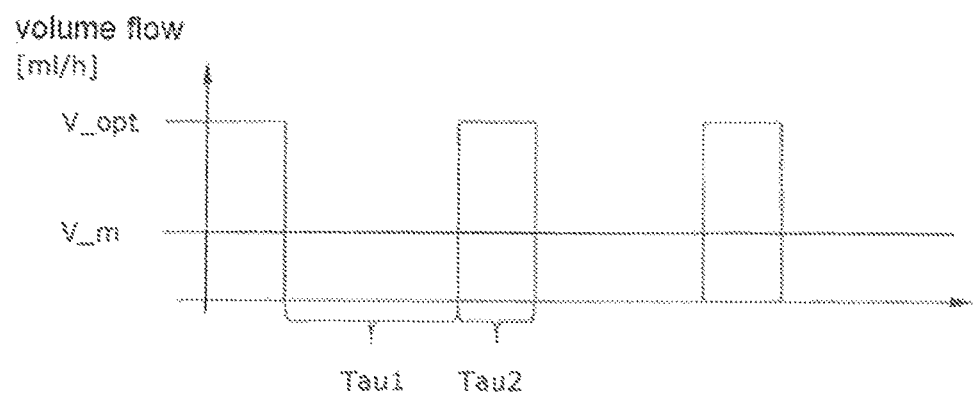
FIG. 2: a diagram of a pulsed flow profile

The control unit 11 controls the blood pump 7 in such a way that the blood is pumped continuously at a predetermined steady flow rate. Depending on the patient or filter, adjustments may be necessary during a treatment. The anticoagulant solution 6 may optionally be pumped continuously or with a pulsed flow profile. The control unit controls the pump 9 for the infusion solution A2, so that it is pumped with a pulsed flow profile. Exemplary embodiments of such pulsed flow profiles are shown in FIGS. 2 and 3, FIG. 2 shows a rippling flow profile in which the pulse widths (Tau2) have a duration of 300 ms.

Figure 3:
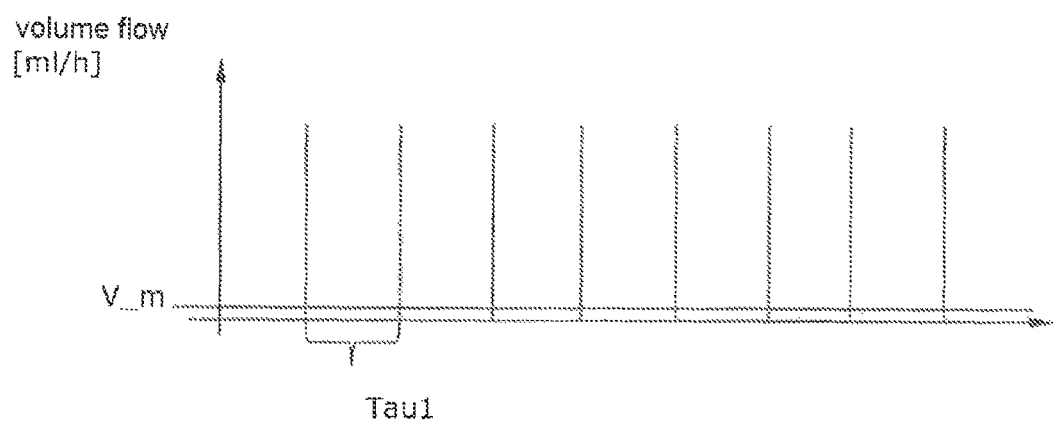
FIG. 3: a diagram of a pulsed flow profile with plug-type pulses

FIG. 3 shows a rippling flow profile where the pulse widths of the pump phases of the pump are very short. This is balanced by a higher frequency f and a higher pulse flow rate. This is where a plug flow develops in the blood. The pulse flow rate here is in the range of the flow rate of the blood pump and higher, e.g., 100 or 500 mL/min.

The frequency is in the range of 20 to 60 $min^{-1}$, but it may be much higher with faster control accordingly.

The method according to the invention ensures an optimized mixture of two solutions in a tubing system. This is especially advantageous in the method of regional anticoagulation with citric acid, where clots may form at the point of addition of the infusion solution that contains calcium. No specially designed addition points are necessary with the method according to the invention and the device according to the invention due to the specific flow profile of the added infusion solution that contains calcium. The optimized mixture is ensured by the treatment machine itself. No special blood tubing systems need be used. However, this method and this device are also advantageous in all situations where an effective mixing of two solutions is the goal.

The invention. being thus described, it will be apparent that the same may be varied in many ways, Such variations are not to be regarded as a departure from the spirit and scope of the invention, and all such modifications as would be recognized by one skilled in the art are intended to he included within the scope of the following claims.

What is claimed is:

1. A method of mixing blood with an infusion solution A in a T-section of a tubing system for an extracorporeal blood treatment, in which the blood, is pumped by a first pump in a main line of the tubing system, and the infusion solution A is pumped by a second pump out of a branch line through the T-section and into the main line, said method comprising:

controlling or regulating the second pump with a control unit such that the second pump runs discontinuously to pump the infusion solution A with a pulsed flow profile associated with a desired dosage thereof, with the control unit calculating the pulsed flow profile for the second pump using a stored algorithm that accounts for a flow rate of the first pump, such that based on an average flow rate (Vm) of the infusion solution A that is associated with the desired dosage, and on an optimal pulse flow rate (Vopt) that occurs in a peak of a pulse of the pulsed profile, which provides for enhanced mixing of the infusion solution A with the blood, the control unit determines a pulse width (Tau2) and a pulse frequency (f) that will provide the enhanced mixing.

2. The method according to claim 1, wherein the control unit controls or regulates the first pump such that the first pump runs continuously to pump the blood at a steady flow rate.

3. The method according to claim 1, further comprising pumping an infusion solution B with a third pump out of an additional branch line and into the main line of the tubing system for the extracorporeal blood treatment.

4. The method according to claim 1, wherein the extracorporeal blood treatment is performed using regional anticoagulation.

5. The method according to claim 3, wherein the infusion solution A is an infusion solution containing calcium, and the infusion solution B is an anticoagulant solution containing citric acid.

6. The method according to claim 3, wherein the control unit controls or regulates the third pump to pump the infusion solution B into the main line.

7. The method according to claim 3, wherein the control unit calculates the pulsed flow profile for the second pump using the stored algorithm that takes into account the flow rate of the third pump.

8. The method according to claim 1, wherein the pulsed flow profile is entered by a user on a user interface and is transmitted to the control unit.

9. The method according to claim 1, wherein the extracorporeal blood treatment is hemodialysis, hemofiltration, and/or hemodiafiltration.

10. A device for extracorporeal blood treatment, said device comprising:
a first pump for pumping blood, a second pump for pumping an infusion solution A, and a control unit,
the control unit controlling or regulating the second pump such that the second pump runs discontinuously to pump the infusion solution A with a pulsed flow profile associated with a desired dosage thereof,
with the control unit calculating the pulsed flow profile for the second pump using a stored algorithm that accounts for a flow rate of the first pump,
such that based on an average flow rate (Vm) of the infusion solution A that is associated with the desired dosage, and on an optimal pulse flow rate (Vopt) that occurs in a peak of a pulse of the pulsed profile, which provides for enhanced mixing of the infusion solution A with the blood, the control unit determines a pulse width (Tau2) and a pulse frequency (f) that will provide the enhanced mixing.

11. The device according to claim 10, wherein the control unit controls or regulates the first pump such that the first pump runs continuously to pump the blood at a steady flow rate.

12. The device according to claim 10, further comprising a third pump for pumping another infusion solution that is an anticoagulant.

13. The device according to claim 12, wherein the control unit controls or regulates the third pump.

14. The device according to claim 12, wherein the control unit calculates the pulsed flow profile for the second pump using the stored algorithm that takes into account the flow rate of the third pump.

15. The device according to claim 14, further comprising a user interface for input of working parameters of at least one of the first pump, the second pump, and the third pump, with the user interface transmitting the working parameters to the control unit.

16. The device according to claim 10, wherein the device is a dialysis machine.

17. The device according to claim 12, wherein the anticoagulant is a citrate.

18. The device according to claim 16, wherein the dialysis machine is a hemodialysis machine, a hemofiltration machine, and/or a hemodiafiltration machine.

* * * * *